United States Patent [19]
Giroldini et al.

[11] Patent Number: 5,597,855
[45] Date of Patent: Jan. 28, 1997

[54] POLY(PENTAERYTHRITYL DIPHOSPHONATE) AND ITS USE IN SELF-EXTINGUISHING THERMOPLASTIC COMPOSITIONS

[75] Inventors: William Giroldini; Antonio Rinaldi, both of S. Donato Milanese; Gianluigi Landoni, Milan; Neri Carlo, S. Donato Milanese, all of Italy

[73] Assignee: Eniricerche S.p.A., Milan, Italy

[21] Appl. No.: 448,879

[22] Filed: May 24, 1995

[30] Foreign Application Priority Data

May 27, 1994 [IT] Italy ................... MI94A1088

[51] Int. Cl.$^6$ .................. C08K 5/34; C08K 3/32; C07F 9/06
[52] U.S. Cl. .............. 524/105; 252/609; 524/415; 524/416; 548/112; 548/334.1
[58] Field of Search .............. 252/609; 524/105, 524/415, 416; 548/112, 307

[56] References Cited

U.S. PATENT DOCUMENTS

| | | | |
|---|---|---|---|
| 3,892,765 | 7/1975 | Porret et al. .............. | 548/112 |
| 3,925,406 | 12/1975 | Porret et al. .............. | 548/112 |
| 4,086,205 | 4/1978 | Birum .................... | 524/120 |

FOREIGN PATENT DOCUMENTS 0530874  3/1993  European Pat. Off. .

*Primary Examiner*—Kriellion S. Morgan
*Attorney, Agent, or Firm*—Oblon, Spivak, McClelland, Maier & Neustadt, P.C.

[57] ABSTRACT

Poly(Pentaerythrityl diphosphonate) of formula (I):

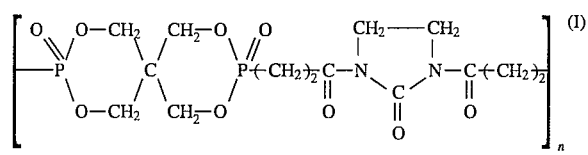

wherein n is an integer having a value comprised within the range of from 3 to 100.

The poly(pentaerythrityl diphosphonate) of formula (I) is useful as a flame retardant additive for thermoplastic polymers.

17 Claims, No Drawings

POLY(PENTAERYTHRITYL DIPHOSPHONATE) AND ITS USE IN SELF-EXTINGUISHING THERMOPLASTIC COMPOSITIONS

The present invention relates to a new poly(pentaerythrityl diphosphonate) and to a process for preparing it.

A further object of the present invention are self-extinguishing thermoplastic polymeric compositions containing a polymer and a self-extinguishing amount of the above said poly(pentaerythrityl diphosphonate).

The production of polymeric compositions displaying high self-extinction values is of considerable moment from the viewpoint of safety, in several application sectors.

In order to endow thermoplastic polymers with flame resistance properties, several flame retardant additives were disclosed in the art, in particular antimony and bismuth oxides and halides, in combination with halogenated organic compounds f such as chlorinated paraffins and polybromoaromatic compounds.

In that way, polymeric compositions are obtained which, although are generally satisfactory as regards their flame retarding characteristics, display drawbacks due to corrosion during the processing step and result to be dangerous during possible combustions owing to their emissions of fumes containing hydrochloric or hydrobromic acid and, sometimes, also traces of polychloro- or polybromo-benzodioxines, which are known to constitute a health risk also when present in small concentrations.

The need for using non-halogenated flame retardant additives capable of overcoming the above described drawbacks, led to the development of other types of additives, among which those which are referred to as "char-forming", which tend to cause the polymer to undergo charring during combustion, with decrease in developed volumes of obscuring fumes and toxicant and corrosive exhaust gases. Such additives are generally used together with ammonium polyphosphate.

In U.S. Pat. No. 4,174,343 the use is disclosed, as flame retardants for olefinic polymers, of mixtures of ammonium polyphosphate and a pentaerythrityl diphosphonate of formula:

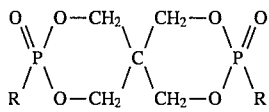

wherein R stands for a methyl, phenyl, benzyl or nitrile group.

In U.S. Pat. No. 4,217,267 self-extinguishing compositions are disclosed which comprise an olefinic polymer, a poly(pentaerythrityl diphosphonate) of

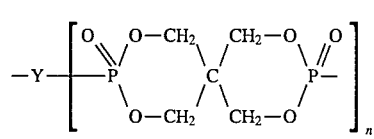

wherein Y stands for a polyolefinic radical possibly substituted with aromatic moieties and n is at least 2; and ammonium polyphosphate.

The main drawbacks displayed by these, as well as other, "char-forming" systems, are their limited heat stability under polymer moulding conditions, the appearance of undesired discolorations and a low hydrolysis stability in the end articles of manufacture.

Therefore, the need exists for having available flame retardant additives which display better characteristics then those as known from the prior art.

The present Applicant has found now a compound which, besides displaying a high heat stability, shows unexpectedly high values of "char-forming" activity, does not cause undesired discolorations to develop and has a high hydrolysis stability in the end articles of manufacture. Furthermore, it can also be used in the absence of other flame retardant additives, and, in particular, in the absence of ammonium polyphosphate or melamine phosphate.

Therefore, the object of the present invention is a poly-(pentaerythrityl diphosphonate) of formula (I):

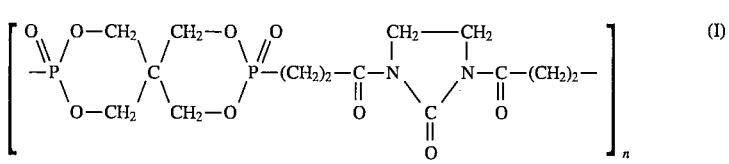

wherein n is an integer comprised within the range of from 3 to 100.

Preferred compound of formula (I) for the purpose of the present invention is that compound in which n is an integer comprised within the range of from 5 to 30.

The compound of formula (I) is useful as a flame retardant additive for thermoplastic polymers.

Poly(pentaerythrityl diphosphonate) of formula (I) has a nearly white or very pale yellow colour, and displays the following characteristics:

it has a very low water solubility (lower than 4% at 20° C.), which depends on the average value of n (in fact, with increasing n values, its solubility decreases);

it is insoluble in such common organic solvents as, e.g., methanol, toluene, acetone;

it is heat stable up to a temperature of about 230° C.;

it displays excellent "char-forming" capabilities.

Poly(pentaerythrityl diphosphonate) of formula (I) can be obtained by means of several processes.

A process for preparing poly(pentaerythrityl diphoshphonate) of formula (I) comprises reacting pentaerythrityl-bis-phosphite of formula

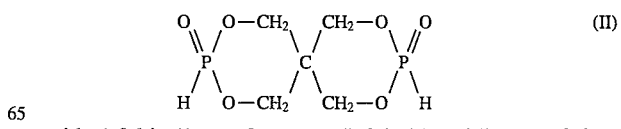

with 1,3-bis-(1-oxo-2-propenyl)-2-imidazolidinone of formula (III):

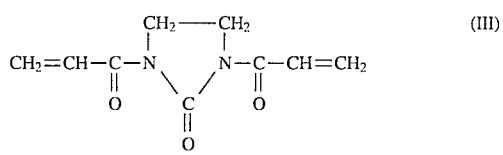

The reaction is carried out in the presence of an organic base to act as a catalyst such as, e.g., tributyl amine, at a temperature comprised within the range of from 120° C. to 180° C., preferably of from 130° C. to 160° C., by initially operating under atmospheric pressure and subsequently under a partial vacuum until a pressure of 20 mm/Hg is reached, during a time of about 6 hours.

The reaction is carried out in the absence of solvents, preferably in a special reactor (e.g., a LIST reactor) capable of supplying an excellent mechanical stirring/milling effect, because the above said reaction mixture rapidly turns into a solid product which must be continuously ground to enable the reaction to go to completion.

The phosphite of formula (II) can be prepared according to the process disclosed, e.g., in U.S. Pat. No. 4,070,336.

The compound of formula (III) can be prepared according to a process which comprises causing the 2-imidazolidinone of formula (IV):

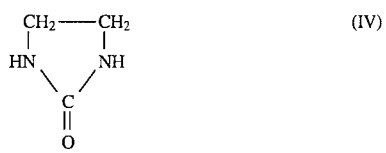

to react with acryloyl chloride of formula (V):

in the presence of such an organic solvent as, e.g., toluene, dioxane, and a catalyst, such as, e.g., hexadecyl-trimethyl-ammonium bromide.

The reaction is carried out at a temperature comprised within the range of from 50° C. to 100° C., preferably of from 60° C. to 85° C., under atmospheric pressure and during a time comprised within the range of from 2 to 3 hours, with hydrochloric acid gas being released. The reaction is finally completed by adding sodium carbonate and water to the raw reaction mixture, in order to favour the dehydrohalogenation of the halogenated byproducts which are formed during the same reaction as, e.g., 1,3-bis-(1-oxo-3-chloro-propano)-2-imidazolidinone.

Poly(pentaerythrityl diphosphonate) of formula (I) can also be prepared according to a process which comprises causing the polyanhydride of formula (VI):

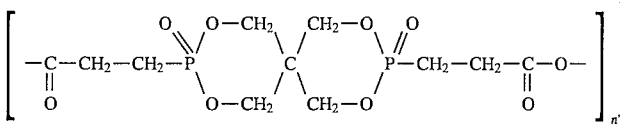

wherein n' is an integer having a value comprised within the range of from 3 to 100, to react with 2-imidazolidinone of formula (IV), in the presence of phosphorus pentoxide ($P_2O_5$) and melamine. The reaction is carried out in the absence of solvents, preferably in a special reactor (e.g., a LIST reactor) capable of supplying an excellent mechanical stirring/milling effect, at a temperature comprised within the range of from 100° C. to 180° C. with a progressive increase in temperature from 100° C. to 180° C. during 4–6 hours, by initially operating under atmospheric pressure and subsequently under a partial vacuum, until a pressure of 20 mm/Hg is reached, with a mixture of poly(pentaerythrityl diphosphonate) of formula (I) and melamine phosphate being thus obtained.

The polyanhydride of formula (VI) can be prepared by causing pentaerythrityl bis(phosphite) of formula (II) to react with acetic anhydride and acrylic acid, in the presence of 2,4-di-t.-butyl phenol acting as an antioxidant agent. The reaction is carried out at a temperature comprised within the range of from 100° C. (initial temperature) up to 140° C. (end temperature), under a pressure comprised within the range of from 120 mm/Hg (initial pressure) down to 20–30 mm/Hg (end pressure) and during a time of about 4 hours. Also in this case, the reaction is preferably carried out in a special reactor (e.g., a LIST reactor) capable of supplying an excellent mechanical stirring/milling effect.

2-Imidazolidinone of formula (IV) is a commercial product.

According to a further aspect, the present invention relates to self-extinguishing thermoplastic polymeric compositions comprising a thermoplastic polymer selected from olefinic polymers or copolymers, linear polyesters, unsaturated polyesters, polyurethanes, acrylonitrile-styrene copolymers (SAN) acrylonitrile-butadiene-styrene terpolymers (ABS), SBR rubbers, and a self-extinguishing amount of poly(pentaerythrityl diphosphonate) of formula (I).

In the above said polymeric compositions poly(pentaerythrityl diphosphonate) of formula (I) is present at a level comprised within the range of from 8% to 25% based on the end polymeric composition, preferably of from 15% to 20%.

The polymeric compositions according to the present invention can contain a blend of poly(pentaerythrityl diphosphonate) of formula (I) with an ammonium polyphosphate, or with a neutral amine phosphate. In this case, the mixture of both said species is contained at a level comprised within the range of from 20% to 40% based on end polymeric composition.

The ratio of poly(pentaerythrityl diphosphonate) of formula (I) to ammonium polyphosphate or amine phosphate can be comprised within the range of from about 2:1 to 1:3.

For the purpose of the present invention, an ammonium polyphosphate of formula (VII) is used:

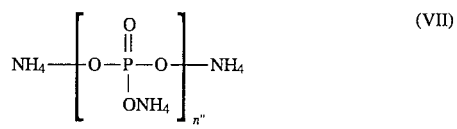

wherein n" is an integer having a value comprised within the range of from 50 to 1000. For example, the commercial products EXOLIT 422 ex Hoechst, or PHOS CHECK P-30 ex Monsanto can be used.

For the purpose of the present invention, said neutral amine phosphate can be selected from melamine phosphate, acetoguanidine phosphate, ethylene diamine phosphate, and so forth.

In the compositions herein, the use of poly(pentaerythrityl diphosphonate) of formula (I) results to be particularly advantageous thanks to the poor solubility of this compound in water and organic solvents, as compared to products of the same type, with polymeric compositions being thus obtained which display self-extinguishing properties that are less damaged by the contact with solvents or water.

Preferred thermoplastic polymers used in the present polymeric compositions are olefinic polymers such as, e.g., low, medium and high density polyethylene, polypropylene and polystyrene; linear polyesters such as, e.g., polyethylene terephthalate; and polybutylene terephthalate, polyurethanes; SB rubbers, such as, e.g., SBR 1502 rubbers filled with carbon black; acrylonitrile-butadiene-styrene (ABS) terpolymers.

The polymeric compositions generally yielding better results are those compositions in which, besides poly(pentaerythrityl diphosphonate) of formula (I), said (co)polymers also contain such ammonium polyphosphates or amine phosphates ad mentioned above.

The self-extinguishing polymeric compositions according to the present invention can additionally contain one or more additives selected, for exemplifying purposes, between antioxidants (sterically hindered phenols, phosphites, thioesters, and so forth), heat and light stabilizers (benzophenones, benzotriazoles, and so forth), metal deactivators (amides with high chelating capabilities, and so forth), basic co-stabilizers (dihydrotalcite, and so forth) and nucleating agents (alkali metal salts of aromatic carboxy acids, and so forth).

The self-extinguishing polymeric compositions according to the present invention can be prepared by using any known means in the art suitable for homogenizing the polymer with the additives.

According to a common procedure in the art, the additive(s) is/are submitted to grinding until it/they is/are reduced to a powder with a particle size comprised within the range of from 1 μm to 200 μm.

The so obtained powder is mixed with the thermoplastic polymer in granular form and such a blend is submitted to extrusion, with granules of the desired self-extinguishing composition being obtained.

For a better understanding of the present invention and in order to practice it, some examples are reported in the following for illustrative, non-limitative purposes.

EXAMPLE 1

Preparation of
1,3-bis(1-oxo-2-propenyl)-2-imidazolidinone of
formula (III).

An amount of 8.6 g (0.1 moles of 2-imidazolidinone of formula (IV), 10 ml of toluene and 0.5 g of hexadecyl-trimethyl-ammonium bromide are charged to a 250 ml-flask equipped with mechanical stirrer, reflux condenser and dropping funnel.

From said dropping funnel, an amount of 19.0 g (0.22 moles of acryloyl chloride is added to the flask during about 10 minutes. Hydrochloric acid gas is developed, which is fixed by absorption with a 10% aqueous sodium hydroxide solution.

The mixture is then kept heated at 85° C. during 3 hours, is cooled down to 20° C., and to it 80 ml of toluene and 50 ml of water are added.

An amount of 12 g of sodium carbonate is slowly added, the mixture is then heated again up to 85° C. and is kept at that temperature during 1 hour and is then cooled down to 20° C.

The resulting raw reaction mixture is charged to a dropping funnel, the organic phase is collected and the aqueous phase is extracted with 50 ml of toluene. The organic phase is then concentrated under vacuum, by operating under a pressure of 20 mm/Hg and at a temperature of 80° C.

Upon cooling, approximately 12 g of product crystallizes off, which is constituted by 1,3-bis(1-oxo-2-propenyl)-2-imidazolidinone of formula (III). The product, which has the appearance of a white crystal powder, was confirmed by mass spectrometry (Hewlett Packard model 5970 spectrometer), and displays an m/z value of 194 (molecular peak).

EXAMPLE 2

Preparation of polyanhydride of formula (VI).

Amounts of 550 g (2.41 moles of pentaerythrityl bis-phosphite of formula (II), 384 g (5.33 moles) of acrylic acid, 538 g (5.27 moles of acetic anhydride and 10 g of 2,4-di-t-butylphenol are charged to a LIST reactor of 2 liters of capacity (a special steel reactor capable of stirring reaction mixtures having extremely high viscosity values).

The reaction mixtures is then heated at the temperature of 100° C. during 3.5 hours, under a pressure comprised within the range of from 80 mm/Hg to 120 mm/Hg in order to distil acetic acid off, however without removing acetic anhydride or acrylic acid.

At the end of the reaction, the temperature is increased up to 140° C. and the pressure is simultaneously reduced down to 30 mm/Hg in order to also distil off acrylic acid and acetic anhydride excess.

The reaction mass is now very thick and viscous and applies a considerably high mechanical stress to the LIST reactor. After about 1 hour, the reaction mixture turns into a solid material containing variously sized granules, which is continuously ground by the LIST reactor.

Approximately 2 hours later, the reaction mass is cooled and, at room temperature, it becomes a crumbly solid material easily ground by the LIST reactor. The product, constituted by polyanhydride of formula (VI), is finally extracted as an off-white coloured powder material in a yield of about 880 g, including those product amounts which remain sticking to reactor walls and stirring blades.

The amount of distilled material is of approximately 640 g (a mixture of acetic acid, acrylic acid, acetic anhydride).

The resulting polyanhydride of formula (VI) is soluble in sodium carbonate containing water, in which it forms its disodium salt. The P-NMR analysis (Bruker AC 200 spectrometer) of such an alkaline solution displays the presence of a dominant peak (>95%) at about 28.5–29.0 ppm, typical of phosphonates.

EXAMPLE 3

Preparation of poly(pentaerythrityl diphosphonate)
of formula (I).

To a single-neck flask of 250 ml of capacity, there are charged 33 g (0.17 moles)of 1,3-bis(1-oxo-2-propenyl) -2-imidazolidinone of formula (III), 5 ml of tributyl amine and 39 g (0.17 moles of pentaerythrityl bis-phosphite of formula (II).

After thorough mixing, the mixture is heated up to 130° C. and is kept heated at that temperature during 1 hour under atmospheric pressure. The mixture turns from heterogeneous-liquid into rubbery and finally into a solid mass with polymeric structure.

The reaction product is cooled down to 20° C., is crushed and is then ground, and the ground material is then heated again up to 140° C., and is kept heated at that temperature during 2 hours, by operating under a pressure of 100 mm/Hg. The reaction product is then cooled, is ground again and is kept heated at 180° C. for 3 hours, by operating under a residual pressure of 20 mm/Hg.

The product is cooled again down to 20° C., is finely ground and is subsequently purified by cold washing with 200 ml of methanol during 30 minutes with stirring, is then filtered, washed with acetone and is finally dried under vacuum, by operating under a pressure of 20 mm/Hg and at a temperature of 160° C.

Approximately 70 g is obtained of a pale yellow powder constituted by poly(pentaerythrityl diphosphonate) of formula (I). Such a product is insoluble in common organic solvents.

EXAMPLE 4

Preparation of poly(pentaerythrityl diphosphonate) of formula (I) in mixture with melamine phosphate.

A mixture of powders constituted by:

70 g (0.2 moles of polyanhydride of formula (VI)
18 g (0.2 moles of 2-imidazolidinone of formula (IV);
26.5 g (0.21 moles) of melamine; and
10 g (0.07 moles) of phosphoric anhydride;

is finely ground in an electrical mill, is then charged to a single-neck flask of 250 ml of capacity, is progressively heated during 2 hours up to 180° C. by initially operating under atmospheric pressure and then under partial vacuum until a pressure of 20 mm/Hg is reached.

The above said mixture is kept under these conditions (180° C. and 20 mm/Hg) for 4 hours. Every 40 minutes the flask is opened, without cooling, the mixture is manually mixed, then vacuum is restored.

After cooling down to 20° C., the resulting solid product is ground again, is cold washed during 20 minutes with 200 ml of methanol with stirring, is subsequently filtered, washed with acetone and vacuum dried at 160° C., by operating under a pressure of 20 mm/Hg.

Approximately 110 g is obtained of a pale yellow powder constituted by 70% of poly(pentaerythrityl diphosphonate) of formula (I) and 30% of melamine phosphate.

EXAMPLE 5

Formulations of poly(pentaerythrityl diphosphonate) of formula (I) with various polymers.

In order to evaluate the self-extinguishing capabilities of the polymeric compositions according to the present invention, some formulations were prepared which contain various types of polymers and poly(pentaerythrityl diphosphonate) of formula (I) either alone, or in mixture with ammonium polyphosphate or melamine phosphate.

Such formulations are extruded through a single screw extruder having a diameter of 30 mm and a length of 1050 mm, with an increasing temperature profile from 190° C. to 220° C., and are then converted into pellet form. The pellets are then moulded to yield small plates of ⅛ inch (3 mm) of thickness, from which specimens are obtained conforming with as required by ASTM D-2863-77 and Underwriters Laboratories, Test UL94, Vertical Test Method (3.10–3.15, September 1973) flammability tests.

By means of ASTMD-2863-77 test, the flammability of a polymeric material is determined as a function of volumetric oxygen concentration. Such a dependance is expressed as L.O.I., i.e., as that minimal oxygen percent content which is capable of supporting the combustion of the specimen in an oxygen-nitrogen atmosphere impinging onto the same specimen by flowing from down upwards (to high L.O.I. values, good self-extinguishment properties correspond).

By means of UL94 test, on the contrary, the behaviour of specimens in the presence of a flame is evaluated. These specimens are classified in order of decreasing self-extinguishing properties according to the rating scale: V-0, V-1 and V-2.

The compositions of the samples and the test results are reported in following Table 1.

TABLE 1

| Polymer | Compound (I) | A.P. | M.P. | ANTIOX | L.O.I. | UL 94 |
|---------|--------------|------|------|--------|--------|-------|
| PP 75%  | 10.0%        | 14.0%| —    | 1%     | 29.0   | V–O   |
| PE 65%  | 17.9%        | 17.0%| —    | 1%     | 27.0   | V–O   |
| TPU 79% | 8.3%         | 11.7%| —    | 1%     | 30.7   | V–O   |
| PP 75%  | 10.0%        | 9.6% | 4.3% | 1%     | 31.8   | V–O   |
| PE 65%  | 14.3%        | 13.6%| 6.1% | 1%     | 30.5   | V–O   |
| PP 74%  | 25.0%        | —    | —    | 1%     | 28.2   | V–O   |
| PP 79%  | 20.0%        | —    | —    | 1%     | 25.7   | V–O   |
| ABS 60% | 14.0%        | 19.0%| 6.0% | 1%     | 31.2   | V–O   |

PP = polypropylene.
PE = polyethylene.
TPU = thermoplastic polyurethane.
ABS = acrylonitrile-butadiene-styrene copolymer.
COMPOUND (I) = poly(pentaerythrityl diphosphonate) of formula (I).
A.P. = ammonium polyphosphate.
M.P. = melamine phosphate.
ANTIOX = 0.5% of ANOX 20 [corresponding to tetrakis methylene-3,5-di-t.-butyl-4-hydroxy-hydrocinnamate)methane ex EniChem Synthesis] and 0.5% of ALKANOX 240 [corresponding to tris(2,4-di-t.-butyl-phenyl)phosphite ex Eni-Chem Synthesis].

We claim:

1. Poly(pentaerythrityl diphosphonate) of formula (I):

$$\left[ \begin{array}{c} O \\ \diagdown \diagup \\ P \\ \diagup \diagdown \\ O-CH_2 \end{array} \begin{array}{c} O-CH_2 \\ \diagdown \\ C \\ \diagup \\ CH_2-O \end{array} \begin{array}{c} CH_2-O \\ \diagdown \diagup \\ P-(CH_2)_{\overline{2}}C-N \\ \diagup \\ O \end{array} \begin{array}{c} CH_2---CH_2 \\ | \quad | \\ N-C-(CH_2)_{\overline{2}} \\ \diagup \\ C \\ \| \\ O \end{array} \right]_n \quad (I)$$

wherein n is an integer comprised within the range of from 3 to 100.

2. Poly(pentaerythrityl diphosphonate) according to claim 1, in which n is an integer having a value comprised within the range of from 5 to 30.

3. Flame retardant additive for thermoplastic polymers, constituted by poly(pentaerythrityl diphosphonate) of formula (I):

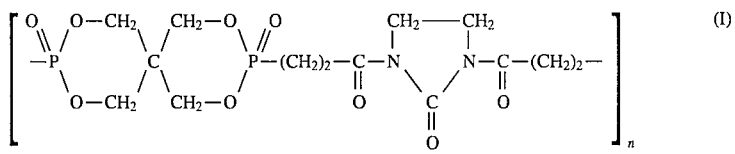

wherein n is an integer comprised within the range of from 3 to 100.

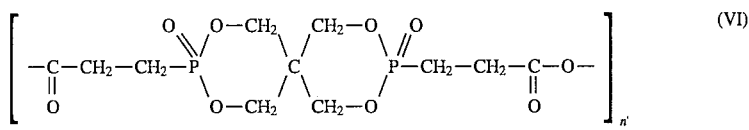

4. Flame retardant additive according to claim 3, in which n is an integer having a value comprised within the range of from 5 to 30.

5. Process for preparing poly(pentaerythrityl diphosphonate) of formula (I) according to any of the preceding claims from 1 to 4, which comprises reacting pentaerythrityl bis-(phosphite) of formula (II):

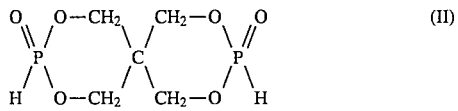

with 1,3-bis-(1-oxo-2-propenyl)-2-imidazolidinone of formula (III):

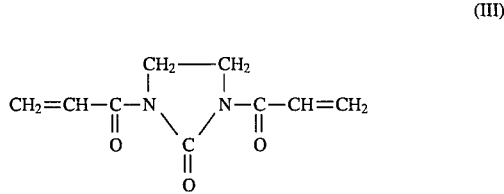

in the presence of an organic base as catalyst, at a temperature comprised within the range of from 120° C. to 180° C., by initially operating under atmospheric pressure and subsequently under a partial vacuum until a pressure of 20 mm/Hg is reached, during a time of about 6 hours, in the absence of solvents and while simultaneously submitting the reaction mixture to a good mechanical stirring/milling effect.

6. Process for preparing poly(pentaerythrityl diphosphonate) of formula (I) according to any of the preceding claims from 1 to 4, which comprises causing the polyanhydride of formula (VI):

wherein n' is an integer having a value comprised within the range of from 3 to 100, to react with 2imidazolidinone of formula (IV):

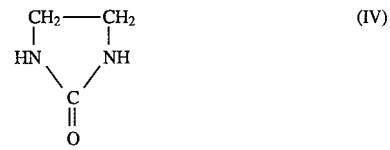

in the presence of phosphorus pentoxide ($P_2O_5$) and melamine, in the absence of solvents, at a temperature comprised within the range of from 100° C. to 180° C. with temperature being progressively increased from 100° C. to 180° C. during 4–6 hours, by initially operating under atmospheric pressure and subsequently under a partial vacuum, until a pressure of 20 mm/Hg is reached.

7. Self-extinguishing thermoplastic polymeric compositions comprising a thermoplastic polymer and a self-extinguishing amount of poly(pentaerythrityl diphosphonate) of formula (I):

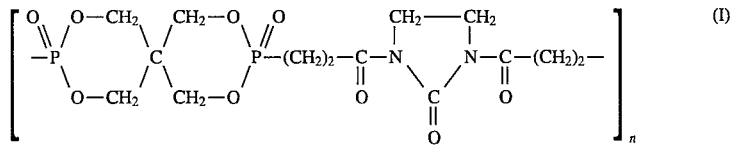

wherein n is an integer comprised within the range of from 3 to 100.

8. Polymeric compositions according to claim 7, in which the thermoplastic polymer is selected from olefinic polymers or copolymers, linear polyesters, unsaturated polyesters, polyurethanes, acrylonitrile-styrene copolymers (SAN), acrylonitrile-butadiene-styrene terpolymers (ABS), SBR rubbers.

9. Polymeric compositions according to claim 8, in which the thermoplastic polymer is selected from low, medium and high density polyethylene, polypropylene and polystyrene; polyethylene terephthalate and polybutylene terephthalate, polyurethanes; SBR 1502 rubbers filled with carbon black; acrylonitrile-butadiene-styrene (ABS) terpolymers.

10. Polymeric composition according to claim 7, in which poly(pentaerythrityl diphosphonate) of formula (I) is present at a level comprised within the range of from 8% to 25% based on end polymeric composition.

11. Polymeric composition according to claim 10, in which poly(pentaerythrityl diphosphonate) of formula (I) is present at a level comprised within the range of from 15% to 20% based on end polymeric composition.

12. Polymeric compositions containing a mixture of poly(pentaerythrityl diphosphonate) of formula (I):

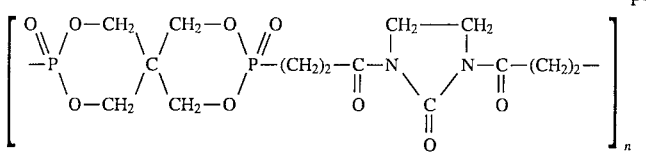

wherein n is an integer having a value comprised within the range of from 3 to 100, with an ammonium polyphosphate or a neutral amine phosphate.

13. Polymeric compositions according to claim 12, in which the blend of poly(pentaerythrityl diphosphonate) of formula (I) with an ammonium polyphosphate or a neutral amine phosphate is contained at a level comprised within the range of from 20% to 40%, based on end composition.

14. Polymeric compositions according to claim 12 or 13, in which the ratio of poly(pentaerythrityl diphosphonate) of formula (I) to ammonium polyphosphate or amine phosphate is comprised within the range of from about 2:1 to 1:3.

15. Polymeric compositions according to any of claims from 12 to 14, in which the ammonium polyphosphate has formula (VII):

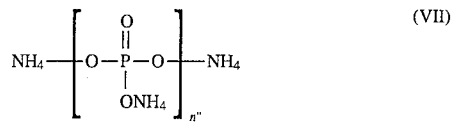

wherein n" is an integer comprised within the range of from 50 to 1000.

16. Polymeric compositions according to any of claims from 12 to 14, in which the neutral amine phosphate can be selected from melamine phosphate, acetoguanidine phosphate, ethylene diamine phosphate.

17. Method for turning a thermoplastic polymer selected from olefinic polymers or copolymers, linear polyesters, unsaturated polyesters, polyurethanes, acrylonitrile-styrene copolymers (SAN), acrylonitrile-butadiene-styrene terpolymers (ABS), SBR rubbers, into a flame resistant one, which method comprises adding to said polymer a self-extinguishing amount of poly(pentaerythrityl diphosphonate) of formula (I):

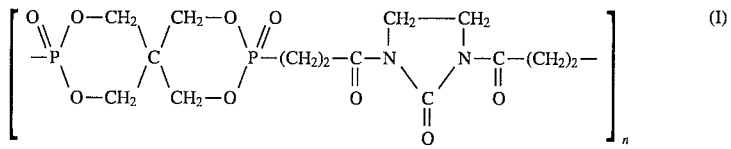

wherein n is an integer having a value comprised within the range of from 3 to 100.

* * * * *